United States Patent [19]

Chen et al.

[11] Patent Number: 5,202,258
[45] Date of Patent: Apr. 13, 1993

[54] IMMUNOSUPPRESSANT-PRODUCING CULTURE

[75] Inventors: Shieh-Shung T. Chen, Morganville; Byron H. Arison, Watchung; George M. Garrity, Westfield; Edward S. Inamine, Rahway, all of N.J.; Sagrario Mochales, Madrid, Spain; Linda S. Wicker, Westfield, N.J.

[73] Assignee: Merck & Co., Inc., Rahway, N.J.

[21] Appl. No.: 847,873

[22] Filed: Mar. 9, 1992

Related U.S. Application Data

[63] Continuation of Ser. No. 637,998, Jan. 4, 1991, abandoned, which is a continuation of Ser. No. 229,365, Aug. 5, 1988, abandoned.

[51] Int. Cl.$^5$ .......................... C12N 1/20; C12R 1/045
[52] U.S. Cl. ................................. 435/252.6; 436/827
[58] Field of Search ................... 435/252.1, 252.6, 827

[56] References Cited

U.S. PATENT DOCUMENTS 4,981,792  1/1991  Inamine et al. ..................... 435/119

FOREIGN PATENT DOCUMENTS 0184162  6/1986  .
0349049  6/1989  European Pat. Off. .
0349061  6/1989  European Pat. Off. .

OTHER PUBLICATIONS

Arai, T., et al. (1962) J. Antibiotics 15, 231–232.

Primary Examiner—Charles L. Patterson, Jr.
Attorney, Agent, or Firm—Robert J. North; Charles M. Caruso

[57] ABSTRACT

Described is a new microorganism, Actinoplanacete sp., (Merck Culture Collection MA 6559) ATCC No. 53771. The microorganism acts as a demethylating agent and can produce the new immunosuppressants, "demethomycin" (L-682,993) a C-31 demethylated analog of L-679,934, and "demethimmunomycin" (L-683,742) a C-31 demethylated analog of L-683,590, under novel fermentation conditions. These macrolide immunosuppressants are useful in preventing human host rejection of foreign organ transplants, e.g. bone marrow and heart transplants.

1 Claim, No Drawings

IMMUNOSUPPRESSANT-PRODUCING CULTURE

This is a continuation of application Ser. No. 07/637,998, filed on Jan. 4, 1991, which is a continuation of application Ser. No. 07/229,365, filed Aug. 5, 1988, both now abandoned.

BACKGROUND OF THE INVENTION

1. Field of the Invention

This invention relates to a new microorganism Actinoplanacete sp., (MA 6559) ATCC No. 53771, which can produce the new immunosuppressant agents, "demethomycin" (L-682,993; also described as 31-desmethoxy-31-hydroxy-L-679,934) and "demethimmunomycin" (L-683,742: also described as 31-desmethoxy-31-hydroxy-L-683,590). The immunosuppressants are produced by culturing the microorganism, with L-679,934 or L-683,950, under conditions which demethylates the respective $C_{31}$ methoxy group of L-679,934 or L-683,950.

2. Brief Description of Disclosures in the Art

In 1983, the U.S. FDA licensed cyclosporin, an extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more effective than cyclosporin. The macrolide is produced by fermentation of a particular strain of *Streptomyces tsukubaensis*. Also described is the closely related macrolide immunosuppressant FK-520, produced by *S. hygroscopicus* subsp. *yakushimaensis*.

U.S. Pat. No. 3,244,592 to T. Arai describes the culturing of *Streptomyces hygroscopicus var. ascomyceticus* to produce the antifungal "ascomycin".

There is, however, no description in the literature of the production of any immunosuppressive agents, which substantially lack the side effects of cyclosporin.

Newer, safer drugs exhibiting less side effects are constantly being searched for in the field.

SUMMARY OF THE INVENTION

It has been found that the new immunosuppressants, "demethomycin", and "demethimmunomycin" can be obtained by the fermentation of the microorganism Actinoplanacete sp., ATCC No. 53771, with the macrolide immunosuppressant L-679,934, or L-683,590, respectively, under submerged aerobic conditions in an aqueous carbohydrate medium, containing a nitrogen nutrient, said conditions being conducted at a pH of about 7 which are sufficient to selectively demethylate L-679,934 or L-683,590 at their respective C-31 positions.

The resultant "demethomycin" and "demethimmunomycin" exhibit immunosuppressive activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay".

The principle of this assay is to measure the proliferation of mouse T lymphocytes stimulated with the combination of ionomycin plus PMA. A positive sample in this assay will inhibit T-cell proliferation, as indicated by reduced tritiated thymidine uptake.

In accordance with this invention, there is provided a biologically pure culture of Actinoplanacete sp., MA 6559, ATCC No. 53771.

DETAILED DESCRIPTION OF THE INVENTION AND PREFERRED EMBODIMENTS

The present invention involves a biologically pure culture of the microorganism Actinoplanacete sp., MA 6559, ATCC No. 53771. The microorganism is currently on restricted deposit with the American Type Culture Collection, 12301 Parklawn Drive in Rockville, Md. as ATCC No. 53771, and in the Merck Culture Collection in Rahway, N.J. as MA 6559. The physical characteristics and taxonomy, including morphological, cultural, biological and physiological characteristics are briefly described hereinbelow.

On the basis of the taxonomic analysis performed thus far, the culture has been tentatively assigned in the order Actinomycetales and in the family Actinoplanacea. Further taxonomic characteristics are being examined to place this organism conclusively within a genus and species.

This culture grows well on routine media including trypticase soy agar (28° and 37° C.), yeast malt extract agar, glycerol asparagine agar, inorganic salt starch agar, oatmeal agar, Czapek Dox, solution and peptone agars and Bennett's agar, all at 28° C.

Morphology—This culture grows as a branched filamentous mycelium with a diameter of 0.2–0.4 microns. Colonies are opaque, raised, and erose. Colony texture is rubbery on yeast malt extract agar but tends to be butyrous on other media where significant fragmentation of the mycelium is observed. The colony surface tends to be powdery in appearance. No diffusable pigments were observed.

Sporangia—are predominantly spherical and range in size from 4–25 microns in diameter. Sporangia are generally visible by 21 days and tend to coalesce on glycerol asparagine agar. Spores are rod-shaped with blunt ends (0.76×1.98 microns), non-motile and occur in long, unbranched chains of up to 150 microns in length.

CULTURAL CHARACTERISTICS OF MA 6559

Yeast Extract-Malt Extract Agar (ISP Medium 2)

Vegetative mycelium is hyaline to yellow, aerial mycelium develops in 24–72 h and is buff to rose-pink and powdery in appearance. The reverse side is tan to reddish brown.

Oatmeal Agar (ISP Medium 3)

Vegetative mycelium is hyaline to yellow, the reverse side is hyaline to tan. Aerial growth is white to light rose-beige and powdery in appearance.

Inorganic Salts-Starch Agar

(ISP Medium 4)

Light growth, scant aerial mycelium. Vegetative growth is hyaline and highly fragmented. Clearing of starch occurs at periphery of colonies noted by 7 d.

Glycerol Asparagine Agar

(ISP Medium 5)

Vegetative growth is hyaline to yellow, the reverse side is hyaline to cinnamon brown. Aerial mycelium is powdery and white to rose-pink.

Peptide-Iron-Yeast Extract Agar

(ISP Medium 6)

Vegetative growth is tan. No aerial growth observed, no melanoid pigments produced.

Tyrosine Agar

(ISP Medium 7)

Vegetative growth is tan becoming deep purple as culture ages. Aerial mycelium is velvety to grayed rose-beige.

Czapek-Dox Agar

Vegetative growth is tan with a pink tone as the culture ages. Aerial mycelia are short and matted with a moist appearance.

The present invention microorganism can be utilized to produce the new immunosuppressants "demethomycin" and "demethimmunomycin", respectively, as disclosed in the following U.S. copending patent applications, also assigned to Merck & Co., Inc. and hereby incorporated by reference for this particular purpose:

Ser. No. 213,063, filed Jun. 29, 1988, now U.S. Pat. No. 4,981,792, which claims a new immunosuppressant, "demethomycin" (L-682,993) a C-31 demethylated analog of L-679,934, produced under novel fermentation conditions utilizing the microorganism, Actinoplanacete sp., (Merck Culture Collection MA 6559) ATCC No. 53771; and Ser. No. 213,025, filed Jun. 29, 1988, now abandoned which claims a new immunosuppressant agent, "demethimmunomycin" (L-683,742) a C-31 demethylated analog of L-683,590 produced under novel fermentation conditions, utilizing the microorganism Actinoplanacete sp. (MA 6559), ATCC No. 53771.

The L-679,934 starting material can be obtained by the fermentation of S. tsukubaensis, (to produce FR-900506, or "FK-506", which is identical to L-679,934) as described in EPO Publication No. 0184162 to Fujisawa, hereby incorporated by reference for this particular purpose, or by the fermentation under the same conditions described in EPO Publication No. 0184162 for producing FR-900506, of Actinoplanacete sp. (Merck Culture Collection MA 6548) ATCC No. 53770, on restricted deposit with the American Type Culture Collection in Rockville, Md.

The L-683,590 starting material can be obtained by the fermentation of S. hygroscopicus var. ascomyceticus, ATCC No. 14891, as described in U.S. Pat. No. 3,244,592, and by the fermentation of S. hygroscopicus subsp. yakushimaensis No. 7278, (to produce FR-900520, or "FK-520", which is identical to L-683,590) as described in EPO Publication No. 0184162 to Fujisawa, said above references hereby incorporated by reference for this particular purpose.

The following examples are given for the purpose of illustrating the present invention and should not be construed as being limitations on the scope or spirit of the instant invention.

EXAMPLE 1

Microorganism and Culture Conditions

The lyophilized culture ATCC No. 53771 was used to inoculate a 250 ml baffled shake flask containing 50 ml of an autoclaved (sterilized) seed medium consisting of (in units of grams/liter) dextrin 10.0%, dextrose 1.0%, beef extract 3.0%, ardamine PH (Yeast Products, Inc.) 5.0%, N-Z Amine type E 5.0%, $MgSO_4.7H_2O$ 0.05%, $KH_2PO_4$ 0.37%, and $CaCO_3$ 0.5%. The pH of the seed medium was adjusted to 7.1 before autoclaving. The seed was incubated in the seed medium at 27° C. for 48 hours on a rotary shaker operating at 220 rpm. Alternatively, when frozen vegetative mycelia or a slant source is used, the culture is incubated in the seed medium at 27° C. for 24 hours at 220 rpm. A 2.5 ml aliquot of the resulting seed medium was used to inoculate a 250 ml non-baffled shake flask containing 50 ml of each of the following two different previously autoclaved (sterilized) production media. L-679,934 was added as a solution in dimethylsulfoxide to achieve a final concentration of 0.1 mg/ml concentration. The shake flask contents were subsequently incubated for 16 hours at 27° C. on a rotary shaker operating at 220 rpm:

1. Transformation medium B consisted of (in grams/liter) glucose 10.0; Hycase SF 2.0; beef extact 1.0; corn steep liquor 3.0; where the pH was adjusted to 7.0 before autoclaving.

2. Transformation medium C consisted of (in grams/liter) mannitol 5.0, glycerol 5.0, Hycase SF 2.0, beef extract 1.0, corn steep liquor 3.0, where the pH was adjusted to 7.0 before autoclaving.

Isolation and Purification Procedure for Each Broth

The whole broth (100 ml) of transformation media B was extracted three times with methylene chloride (3×100 ml). Methylene chloride extracts were combined, dried over sodium sulfate, and concentrated under vacuum to an oily residue. The residue was dissolved in acetonitrile and subjected to high performance liquid chromatography (HPLC) purification.

HPLC was carried out on Whatman Partisil 10 ODS-3, 4.6 mm×25 cm column and monitored at 205 nm and 225 nm at 60° C. The column was developed with linear gradient from 0.1% aqueous $H_3PO_4$—$CH_3CN$, 45:55 to 0.1% aqueous $H_3PO_4$—$CH_3CN$, 20:80 in 30 minutes. The compound was collected during repeated injections of the above described extract. The fractions at retention time 14 minutes were pooled, adjusted to pH 6.5 and evaporated to remove acetonitrile. The compound was further purified using a $C_{18}$ Sep-Pak (Waters Associates) and acetonitrile-water elution solvent to yield 1 mg. The compound was designated as L-682,993, "demethomycin". Similar results were obtained by the use of transformation medium C.

EXAMPLE 2

T-Cell Proliferation Assay

1. Sample Preparation

Purified demethomycin, as prepared by HPLC above, was dissolved in absolute ethanol at 1 mg/ml.

2. Assay

Spleens from C57Bl/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$ M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The control, being the medium without test drug, and various below-indicated dilutions of the sample (above-described purified demethomycin) to be tested were then added in triplicate wells at 20 μl/well. L-679,934 was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as percent inhibition of tritiated thymidine uptake (proliferation) as follows:

$$\% \text{ Inhibition} = 100 - \frac{\text{Mean cpm sample tested}}{\text{Mean cpm control medium}} \times 100.$$

The results of % inhibition at various concentrations of demethomycin are presented in the following Table:

TABLE

| Inhibition of T-Cell Proliferation by Demethomycin | |
|---|---|
| Demethomycin (ng/ml) | % Inhibition |
| 5 | 98.1 |
| 3.3 | 97.2 |
| 2.2 | 92.9 |
| 1.5 | 80.5 |
| 0.99 | 67.1 |
| 0.66 | 36.8 |
| 0.44 | 0 |
| 0.29 | 0 |

Notes:
1. Mouse T cell cultures were pulsed with $^3$H-thymidine for 4 hours prior to harvesting at 48 hours.
2. Standard L-679,934 (10 ng/ml) gave 99% inhibition.
3. $IC_{50}$ = 0.86 ng/ml = 1.09 nM, for demethomycin (L-682,993), and generally in the range 0.6 to $1.2 \times 10^{-9}$ M.
4. Inhibition of T-cell proliferation by demethomycin was reversed by the addition of 50 μ/ml of IL-2 (recombinant IL-2) at the initiation of culture.

EXAMPLE 3

Microorganism and Culture Conditions

The lyophilized culture (MA 6559) ATCC No. 5371 was used to inoculate a 250 ml baffled shake flask containing 50 ml of an autoclaved (sterilized) seed medium consisting of (in units of grams/liter) dextrin 10.0%, dextrose 1.0%, beef extract 3.0%, ardamine PH (Yeast Products, Inc.) 5.0%, N-Z Amine type E 5.0%, $MgSO_4.7H_2O$ 0.05%, $KH_2PO_4$ 0.37%, and $CaCO_3$ 0.5%. The pH of the seed medium was adjusted to 7.1 before autoclaving. The seed was incubated in the seed medium at 27° C. for 48 hours on a rotary shaker operating at 220 rpm. Alternatively, when frozen vegetative mycelia or a slant source is used, the culture is incubated in the seed medium at 27° C. for 24 hours at 220 rpm. A 2.5 ml aliquot of the resulting seed medium was used to inoculate a 250 ml non-baffled shake flask containing 50 ml of the following previously autoclaved (sterilized) transformation medium B. L-683,590 was added as a solution in dimethylsulfoxide to achieve a final concentration of 0.1 mg/ml concentration. The shake flask contents were subsequently incubated for 18 hours at 27° C. on a rotary shaker operating at 220 rpm:

1. Transformation medium B consisted of (in grams/liter) glucose 10.0; Hycase SF 2.0; beef extract 1.0; corn steep liquor 3.0; where the pH was adjusted to 7.0 before autoclaving.

Isolation and Purification Procedure for the Broth

The whole broth (100 ml) of transformation media B was extracted three times with methylene chloride $(3 \times 100 \text{ ml})$. Methylene chloride extracts were combined, dried over sodium sulfate, and concentrated under vacuum to an oily residue. The residue was dissolved in acetonitrile and subjected to high performance liquid chromatography (HPLC) purification.

HPLC was carried out on Whatman Partisil 10 ODS-3, 9.4 mm $\times$ 25 cm column and monitored at 205 nm and 225 nm at 60° C. The column was developed with linear gradient from 0.1% aqueous $H_3PO_4$—$CH_3CN$, 45:55 to 0.1% aqueous $H_3PO_4$—$CH_3CN$, 20:80 in 30 minutes. The compound was collected during repeated injections of the above described extract. The fractions at retention time 24 minutes were pooled, adjusted to pH 6.5 and evaporated to remove acetonitrile. The compound was further purified using a $C_{18}$ Sep-Pak (Waters Associates) and acetonitrile-water elution solvent to yield 1.4 mg. of product, designated as L-683,422, "demethimmunomycin". Similar results were obtained by the use of transformation medium C.

EXAMPLE 4

T-Cell Proliferation Assay

1. Sample Preparation

Purified demethimmunomycin, as prepared by HPLC above, was dissolved in absolute ethanol at 1 mg/ml.

2. Assay

Spleens from C57Bl/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$ M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The control, being the medium without test drug, and various below-indicated dilutions of the sample (above-described purified demethimmunomycin) to be tested were then added in triplicate wells at 20 μl/well. L-679,934 was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed a percent inhibition of tritiated thymidine uptake (proliferation) as follows:

$$\% \text{ Inhibition} = 100 - \frac{\text{Mean cpm sample tested}}{\text{Mean cpm control medium}} \times 100.$$

The results of % inhibition at various concentrations of demethimmunomycin are presented in the following Table:

TABLE

Inhibition of T-Cell Proliferation by Demethimmunomycin

| Demethimmunomycin (ng/ml) | % Inhibition |
|---|---|
| 10 | 98.6 |
| 6.6 | 97.9 |
| 4.4 | 91.9 |
| 2.9 | 86.3 |
| 1.9 | 72.1 |
| 1.3 | 38.2 |
| 0.9 | 9.0 |
| 0.6 | 0 |

Notes:
1. Mouse T cell cultures were pulsed with $^3$H-thymidine for 4 hours prior to harvesting at 48 hours.
2. Standard L-679,934 (10 ng/ml) gave 99% inhibition.
3. $IC_{50}$ = 1.4 ng/ml = 1.81 nM, for demethimmunomycin, (L-638,742), and generally in the range of 1.6 to $1.9 \times 10^{-9}$ molar.
4. Inhibition of T-cell proliferation by demethimmunomycin was reversed by the addition of 50 μ/ml of IL-2 (recombinant IL-2) at the initiation of culture.

What is claimed is:

1. A biologically pure culture of Actinoplanacete sp., (MA 6559) ATCC No. 53771.

* * * * *